United States Patent
Mound et al.

(10) Patent No.: US 7,663,108 B2
(45) Date of Patent: Feb. 16, 2010

(54) PULVERIZED BULK MATERIAL PLANETARY AND DOUBLE HELIX ANALYZER SYSTEM

(75) Inventors: Michael Mound, Baden (CH); Leopold Blahous, Wettingen (CH)

(73) Assignee: ABB Schweiz AG (CH)

( * ) Notice: Subject to any disclaimer, the term of this patent is extended or adjusted under 35 U.S.C. 154(b) by 7 days.

(21) Appl. No.: 12/018,517

(22) Filed: Jan. 23, 2008

(65) Prior Publication Data

US 2009/0184249 A1    Jul. 23, 2009

(51) Int. Cl.
  *G01F 23/00*    (2006.01)
  *G01J 3/00*    (2006.01)
(52) U.S. Cl. .................... 250/357.1; 250/358.1; 356/26
(58) Field of Classification Search ............... 250/357.1, 250/432 R, 360.1, 358.1, 343, 326; 356/326
  See application file for complete search history.

(56) References Cited

U.S. PATENT DOCUMENTS

| | | | |
|---|---|---|---|
| 4,026,717 A | | 5/1977 | Harris et al. |
| 4,508,573 A | | 4/1985 | Harris |
| 4,792,234 A | * | 12/1988 | Doherty ........................ 366/14 |
| 4,799,880 A | | 1/1989 | McCoy |
| 4,976,540 A | | 12/1990 | Kitamura et al. |
| 5,475,220 A | * | 12/1995 | Hughes et al. ......... 250/339.09 |
| 5,754,423 A | | 5/1998 | Tuetenberg et al. |
| 5,943,388 A | | 8/1999 | Tümer |
| 6,055,052 A | | 4/2000 | Lilienfeld |
| 6,122,042 A | * | 9/2000 | Wunderman et al. .......... 356/73 |
| 6,160,618 A | | 12/2000 | Garner |
| 6,491,751 B1 | | 12/2002 | Watson |
| 6,709,510 B1 | | 3/2004 | Young et al. |
| 6,771,369 B2 | | 8/2004 | Rzasa et al. |
| 7,310,581 B2 | | 12/2007 | Mound |
| 2003/0123056 A1 | | 7/2003 | Barnes et al. |
| 2004/0031335 A1 | | 2/2004 | Fromme et al. |
| 2004/0207842 A1 | | 10/2004 | Rzasa et al. |
| 2004/0232339 A1 | | 11/2004 | Lanoue |
| 2005/0077471 A1 | | 4/2005 | Edwards et al. |
| 2007/0206186 A1 | * | 9/2007 | Sharma ....................... 356/317 |

(Continued)

FOREIGN PATENT DOCUMENTS

WO    02054048 A1    7/2002

(Continued)

OTHER PUBLICATIONS

Analytical Spectral Devices, Inc.; Field Spectrometry: Techniques and Instrumentation; Boulder, Colorado; 2001; 9 pages.

(Continued)

*Primary Examiner*—David P Porta
*Assistant Examiner*—Yara B Green
(74) *Attorney, Agent, or Firm*—St. Onge Steward Johnston & Reens LLC

(57) ABSTRACT

A system for analyzing a bulk material including a tube for transporting a stream of a bulk material, a plurality of illuminators for directing radiation through the stream and arranged about a circumference of the tube, a plurality of detectors arranged substantially opposite the illuminators, and at least one spectrometer for receiving and analyzing data from the plurality of detectors.

27 Claims, 5 Drawing Sheets

U.S. PATENT DOCUMENTS

| 2007/0263212 | A1 | 11/2007 | Mound |
| 2007/0265783 | A1 | 11/2007 | Mound |

FOREIGN PATENT DOCUMENTS

| WO | 02065072 | A2 | 8/2002 |
| WO | 02065100 | A2 | 8/2002 |
| WO | 02065101 | A2 | 8/2002 |
| WO | 02065102 | A2 | 8/2002 |
| WO | 02088811 | A1 | 11/2002 |
| WO | 2004106874 | A1 | 12/2004 |
| WO | 2006054154 | A1 | 5/2006 |

OTHER PUBLICATIONS

Analytical Spectral Devices, Inc; Quantitative Analysis of Concrete Samples Via NIR; Bolder, Colorado; www.asdi.com; 2004; 7 pages.

Clark, R. N.; Spectroscopy of Rocks and Minerals, and Principles of Spectroscopy, in Manual of Remote Sensing, Chapter 1: vol. 3, Remote Sensing for the Earth Sciences, (A.N. Rencz, ed.) John Wiley and Sons, New York, p. 3-58, 1999; 67 pages.

European Search Report; Oct. 6, 2006; 7 Pages.

Advanced Spaceborne Thermal Emission and Reflection Radiometer; ASTER (Japanese Ministry of Economy, Trade and Industry and NASA); www.asterweb.jpl.nasa.gov; published prior to May 2007, 83 pages, published Aug. 2, 2005.

Analytical Spectral Devices, Inc.; Identification of raw materials by NIR reflectance; Boulder, Colorado; www.asdi.com; published prior to May 2007, 8 pages.

Analytical Spectral Devices, Inc.; Introduction to NIR Technology; Boulder, CO; www.asdi.com; published prior to May 2007, 10 pages.

Analytical Spectral Devices, Inc.; NIR Analysis of White Powder Samples; Boulder, Colorado; www.asdi.com; published prior to May 2007, 4 pages.

CTR Carinthian Tech Research AG; Spectral Imaging Brochure; www.ctr.at; published prior to May 2007, 2 pages.

International Search Report & Written Opinion of the International Searching Authority; PCT/EP2009/050322; Apr. 29, 2009; 11 pages.

Leetham, Darrell, et al.; Flexibility in Online Analysis; USA; www.thermo.com; published prior to May 2007, 6 pages, published Nov. 2004.

Perkinson, Maire-Claire et al.; Low Cost Hyperspectral Imaging From Space; England; published prior to May 2007, 4 pages.

Stevens, Dave et al.; Recent Developments in Hyperspectral Imaging and their Significance as a New and Important Direct Exploration Tool; published prior to May 2007, 26 pages.

* cited by examiner

PULVERIZED BULK MATERIAL PLANETARY AND DOUBLE HELIX ANALYZER SYSTEM

FIELD OF THE INVENTION

The invention relates to a system for bulk material analysis, and more specifically to a system and method for analyzing material in a powder state for industrial applications.

BACKGROUND OF THE INVENTION

Bulk materials are utilized and produced in industrial applications such as cement production, scrap material processing, and process waste handling. Bulk materials can be characterized as materials used in industrial applications that are transported in high volumes on a continuously moving means such as a conveyor belt after the materials are crushed or otherwise reduced in size for purposes of easier handling in downstream production. Bulk materials can further be characterized as raw materials that are combined in proportion and processed to form another material (such as pre-blended materials), the resulting combination of mixed raw materials (such as post-blended materials) in a homogeneous or non-homogeneous form, scrap materials, and process waste. Bulk materials can also be characterized as materials with low unit value (i.e., individual amounts less than one ton in weight have essentially very small commercial values). In order to achieve economical processing, large volumes are transported to the downstream production units where the relatively valuable mineral contents are separated, or the comminution processes reduce the mass to manageable particle sizes for chemical, hydrometallurgical, or pyroprocessing stages. Therefore, no one particle has more or less value than its neighbor (unlike high value particles that undergo separation as with contained precious metals or gemstones from mass materials), and all material is treated "in bulk." Typical bulk materials include heterogeneous masses of coarsely crushed mined or quarried bulk materials such as ores of limestone, bauxite, copper, zinc, lead, iron, silica, phosphate rock, potash, clay, rare earths. Other bulk materials transported similarly include scrap materials, chalk, coal and coke, alumina, marl, pyrite, fly ash, process waste, etc. Such bulk materials are utilized in process streams in which the bulk materials are fed or supplied from a source continuously, in batches, or over an extended period of time.

In some processes that utilize bulk materials, components or raw materials are transported from dispensing sources (such as bins or silos), mixed together, and processed to form a new material. Typically, bulk materials are transported through these processes in large volumes utilizing conveyor belts. Many processes that transport high volumes of bulk materials also use pneumatic tubes or air slides to transfer the bulk materials between process points.

During the transportation and processing of bulk materials, it becomes necessary to analyze the exact or average chemical or mineral content and composition of the bulk material for control purposes. Such analysis is especially necessary when the bulk materials are mixed, ground, or processed to form new materials. In the context of process waste, the characterization of bulk materials can be effective in diagnosing the effectiveness of a process and monitoring for contaminants. Acquiring sufficiently accurate and detailed knowledge of the physical and chemical state of a moving stream of bulk materials can be difficult and challenging.

Cement processing is characterized by the processing and formation of bulk materials. Cement can be formed by mixing and intergrinding different raw material components in the dry condition (dry process) or it may be done in water (wet process). A flow diagram for a cement manufacturing process is depicted in FIG. 1. In this typical version of the cement manufacturing process, one or more feeders 100-102 introduce 110-112 crushed raw components on to conveyor belts 105-107. The type of raw components combined to ultimately form cement depends on the type of cement being produced and the composition of the raw components being utilized. Typical raw components include calcareous materials (such as limestone, marl, chalk, oyster shells, aragonite and the like), argillaceous materials (such as clay, shale, slate, slag, fly ash, sand, sandstone and the like), ferruginous material (such as mill scale, iron ore or pyrites), alumina (such as bauxite or materials high in alumina) and certain additives that contribute to the characteristics of the cement. In some parts of the world, limestone, marls and the like that include the calcareous component may also include sufficient proportions of the argillaceous material, such as aluminum oxide and iron oxide, so that only siliceous materials need to be added. Siliceous materials can similarly contain argillaceous material so that such siliceous material may incorporate the needed aluminum oxides. Each raw component can have a different mass particle size. For instance, one raw component may have a greater relative particle size while another raw component may have a much smaller average particle size. As a result, the overall admixture of these components can differ in terms of different chemistry as well as widely different particle sizes.

The crushed raw components are typically conveyed to a second conveyor belt 115 and admixed 120 on the conveyor belt 115 in predetermined proportions. The proportions in which the raw components are admixed can be controlled by the rate in which the feeders dispense the raw components and the rate at which the first conveyor belts transport the raw components. As a result, each of the raw components is admixed at different rates of quantity per unit time. Table 1 shows the relative mineral composition of a typical admixture:

TABLE 1

| Dry Basis Oxide | Composition Range* (%) |
|---|---|
| $SiO_2$ | 20 (5-25) |
| $Al_2O_3$ | 8 (0-8) |
| $Fe_2O_3$ | 8 (0-8) |
| CaO | 30 (25-55) |
| MgO | 6 (0-6) |
| $K_2O$ | 3 (0-3) |
| $Na_2O$ | 3 (0-3) |
| $SO_3$ | 3 (0-3) |

In dry processing, the admixed raw components are transported through a series of coarse and/or fine grinding mills 125. The mills integrate 135 the raw components into a homogeneous mixture and dispense a coarse granulation, such as between 50 and 100 mesh, or a fine granulation, such as smaller than 100 mesh, respectively. The mills can be any kind of grinding apparatus, such as an industrial roller, rotary mill, ball mill, disc mill, cage mill, muller mill, high speed mill or the like. These mills dispense the resulting raw mixture onto subsequent conveyor belts, pneumatic tubes or air slides 130, which transport the raw mixture to other mills or process stations. Upon completion of the processing of the raw mixture, the raw mixture is conveyed to a kiln 140.

During the transport of the raw components and the raw mixture from the feeders to the kiln other processing steps and apparatuses optionally may be included. These additional steps and apparatuses may be additional crushers, feeders that provide additional additives to the raw mixture, transport belts, storage facilities and the like.

The kiln can be vertically angled and mounted such that it can be rotated about its central longitudinal axis. The raw mixture is introduced at the top (or feed end) of the kiln and transported down the length of the kiln under the force of gravity. The kiln operates at temperatures on the order of 1,000 degrees Celsius. As the raw mixture passes through the kiln, the raw mixture is calcined (reduced, in chemical terms). Water and carbon dioxide are driven off, chemical reactions take place between the components of the raw mixture, and the components of the raw mixture fuse to form what is known as clinker. In the course of these reactions new compounds are formed. The fusion temperature depends on the chemical composition of the feed materials and the type and amount of fluxes that are present in the mixture. The principal fluxes are alumina ($Al_2O_3$) and iron oxide ($Fe_2O_3$), which enable the chemical reactions to occur at relatively lower temperatures.

The clinker thus formed is discharged 150 typically onto a grate-type cooler. The cooled clinker is then transported by conveyor belt, pneumatic tube or air slide 145, where a feeder 155 dispenses and admixes 160 gypsum to the clinker. The mixture is transported to a mill 165, which crushes the clinker and homogeneously mixes the gypsum into the composition forming a fine powder cement composition. The mill 165 dispenses the cement composition onto a conveyor belt 170, 180, 185 or into a transport tube or air slide, that transports 175 the cement to silos 190,195 for storage.

Wet systems involve processing the raw components through suitable crushers, grinders and mills either individually or as an admixed composition to the desired level of fineness. The raw components are then fed into water to form slurry. The slurry is transported to a storage tank for that purpose and is constantly agitated. At this stage the slurry can be tested and additives can be included. The slurry is then reduced to a desired fineness by feeding the slurry through suitable crushers, grinders and mills. The slurry is eventually fed into the kiln and processed as in the dry process procedure.

One important consideration in the creation of cement is that the proportion of components must be maintained within narrow limits. Differences in the amount of components introduced in the raw mixture and differences in the composition of the components formed during processing affect the quality and grade of cement. Other factors that influence the type of cement produced include temperature, residence time, size of the particles, and intimacy of contact between the particles. As a result, care must be taken in making decisions to consider both upstream conditions and predict downstream results when any adjustments are made to the mix of raw components materials in order to achieve the desired result.

Traditionally, analysis and monitoring of either raw material components, blended materials such as the raw mixture, and processed cement has been accomplished by extracting samples from the continuous flow and transporting them either manually or via an automatic "tube post" pneumatic capsule sampling and conveying system from the sampling point to a central laboratory for analysis. The laboratory would then prepare and analyze the samples utilizing a variety of standard equipment and instruments. The results of these analyses are then used to adjust factors such as the rate at which the raw components are proportioned to achieve a desired blend recipe.

This arrangement, while providing high accuracies, is deficient because the aggregate time required for sampling, splitting, transport, preparation, and analysis can vary from a minimum of 15-30 minutes to an hour or more. During this delay, the stream of components and mixtures continue to be processed such that tons of the fast-moving bulk materials represented by each sample analyzed have long passed points of control and adjustment. The path followed by these materials from the feeders, along the conveyor belts, through the grinders and kiln and into the silos is a continuous flow (or stream). Any adjustments subsequently made to the process will not be able to correct deficiencies in raw mixtures and processed cement that have moved beyond positions in which corrective action may be taken. These adjustments will only affect raw components, raw mixtures and processed cement that are generated subsequent to the adjustments.

Another difficulty with the above is that this method does not provide a solution to potential problems that require prompt dynamic corrective actions. For instance, the rate of admixing raw components depends not only on the type of materials being mixed but also on the composition of those components. If a feeder contains raw components that lack compositional uniformity, the sample analysis may not be representative of the current stream. Thus, any adjustments that are made after a sample analysis may not be appropriate for the current components and respective composition of those components.

For instance, U.S. Pat. No. 4,026,717 describes a method for monitoring the production of cement in which samples are taken from the material flow stream at various points along the process. After the samples are processed by a coarse mill, a pre-kiln sampler using a bucket extracts samples every 15 seconds and deposits the samples on a second conveyor belt. The belt transports the samples to a blending mill that collects develops a composite sample over 15 minute time period. A conveyor then transports the composite sample to an x-ray analyzer. These samplers are also disclosed for extracting samples from the kiln and the clinker cooling system.

Analysis of cement bulk materials can also require knowledge of the oxides or mineralogical phases (molecular polymorphs), or a standard calculated module based on the quantity of the oxides (or other desired measured properties) present, for standard quality control. Some analytical devices used may not measure either oxide or actual phases directly, but only the elemental values.

A few methods to achieve elemental, and thereby, oxide forms of the chemical constituents of the various raw or blended materials have been utilized. They are, however, limited in terms of practical application and mainly make use of atomic events based upon neutron activation via nuclear activation. These so-called Prompt Gamma Neutron Activation Analysis (PGNAA) systems require either radioactive isotopes for neutron flux, such as the isotope of Californium, $Cf_{252}$, or a neutron generator (tube). In these cases, the introduced neutrons cause momentary and temporary disequilibrium of the nuclei of contained materials resulting in emission of gamma radiation signatures as a reaction to restore equilibrium. Neutron activation systems apply a potentially hazardous (to humans) technique which requires protective permanent careful shielding to avoid and minimize direct or indirect exposure and frequent costly isotope or generator tube replacements. The short half-life of $Cf_{252}$ at only approximately two and a half years and the requirement for replacement of neutron tube generators, normally every one to one and a half years, represent both expensive maintenance costs as well as the need to address increasing difficulties in convincing authorities of the public safety in transport and operation of both these types of neutron sources. Further, the resultant gamma radiation from the neutron activation of bulk materials that is caused by neutron flux bombardment of the nuclei of the irradiated materials represents potential additional health and environmental hazards. Other on-line techniques that have been attempted, such as high-power X-ray tube systems, or X-ray diffraction systems, may also require strict adherence to local regulatory authorities. In some venues, the presence of certain of these various classes of all of such devices may be restricted or prohibited altogether.

What is desired therefore is a system and method for analyzing bulk materials that provides real-time analyses for rapid and real-time control of the composition of the bulk material. Also desired is such a system and method that does not alter or touch (either physically or chemically) the streaming bulk materials.

SUMMARY OF THE INVENTION

Accordingly, it is an object of the present invention to provide a bulk material analysis system that overcomes the obstacles in the prior art using an array of optical probes in communication with a spectrometer to analyze bulk material in process.

It is a further object of the present invention to provide such a bulk material analysis system particularly adapted for use in a stream of bulk material passing through a tube.

These and other objectives are achieved by providing a system for analyzing a bulk material including a tube for transporting a stream of a bulk material, a plurality of illuminators directing radiation through the stream and arranged about a circumference of the tube, a plurality of detectors arranged substantially opposite the illuminators, and at least one spectrometer for receiving and analyzing data from the plurality of detectors. Each of the plurality of detectors may be optical near infrared probes and arranged opposite of one of the plurality of illuminators.

In some embodiments, each of the plurality of illuminators and each of the plurality of detectors are arranged substantially within a cross-section of the tube perpendicular to a center axis of the tube. In some embodiments, the plurality of detectors are arranged in a first helix extending along a length of the tube and the plurality of illuminators are arranged in a second helix extending along the length.

In other embodiments, each of the plurality of illuminators is substantially adjacent to at least one of the detectors and the plurality of detectors and the plurality of illuminators are arranged in two or more substantially opposite helical arrangements about the tube.

Further provided is a method for real-time analysis of a bulk material, including the steps of receiving a stream of a bulk material via a tube, providing illumination across at least a portion of the stream via an array of illuminators arranged about a circumference of the tube, receiving at least some of the illumination via plurality of detectors arranged substantially opposite of the illuminators, and providing data indicative of the illumination received via the detectors to at least one spectrometer for analysis.

Other objects, features and advantages according to the present invention will become apparent from the following detailed description of certain advantageous embodiments when read in conjunction with the accompanying drawings in which the same components are identified by the same reference numerals.

DETAILED DESCRIPTION OF THE INVENTION

The present invention will now be described more fully hereinafter with reference to the accompanying drawings which illustrate preferred embodiments of the invention. This invention may, however, be embodied in many different forms and should not be construed as limited to those set forth herein. Rather, these embodiments are provided so that this disclosure will be thorough and complete, and will fully convey the scope of the invention to those skilled in the art. Like numbers refer to like elements throughout.

Figure 1:
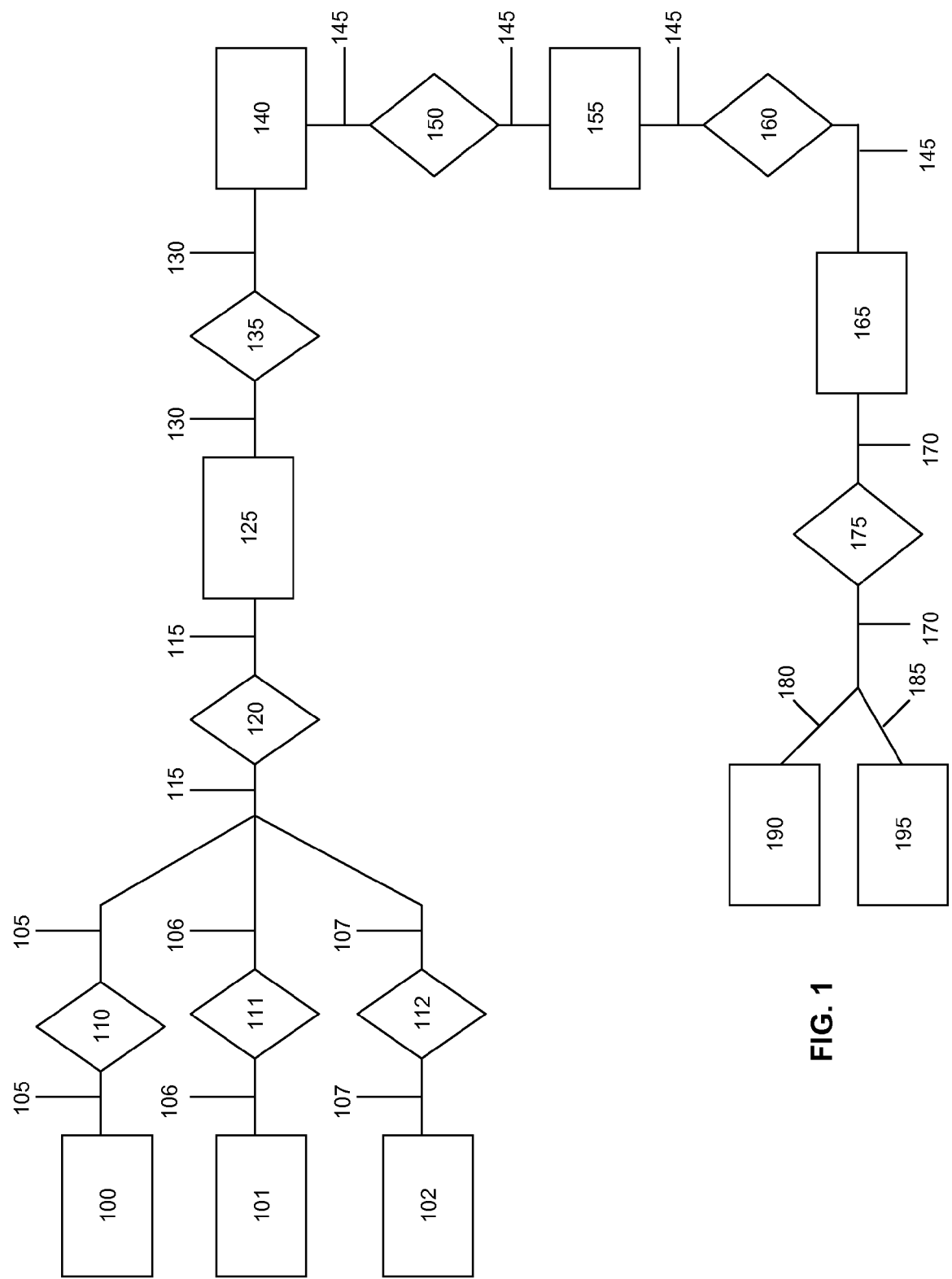
FIG. 1 is flow chart depicting the process steps of a common method for manufacturing cement.
Figure 2:
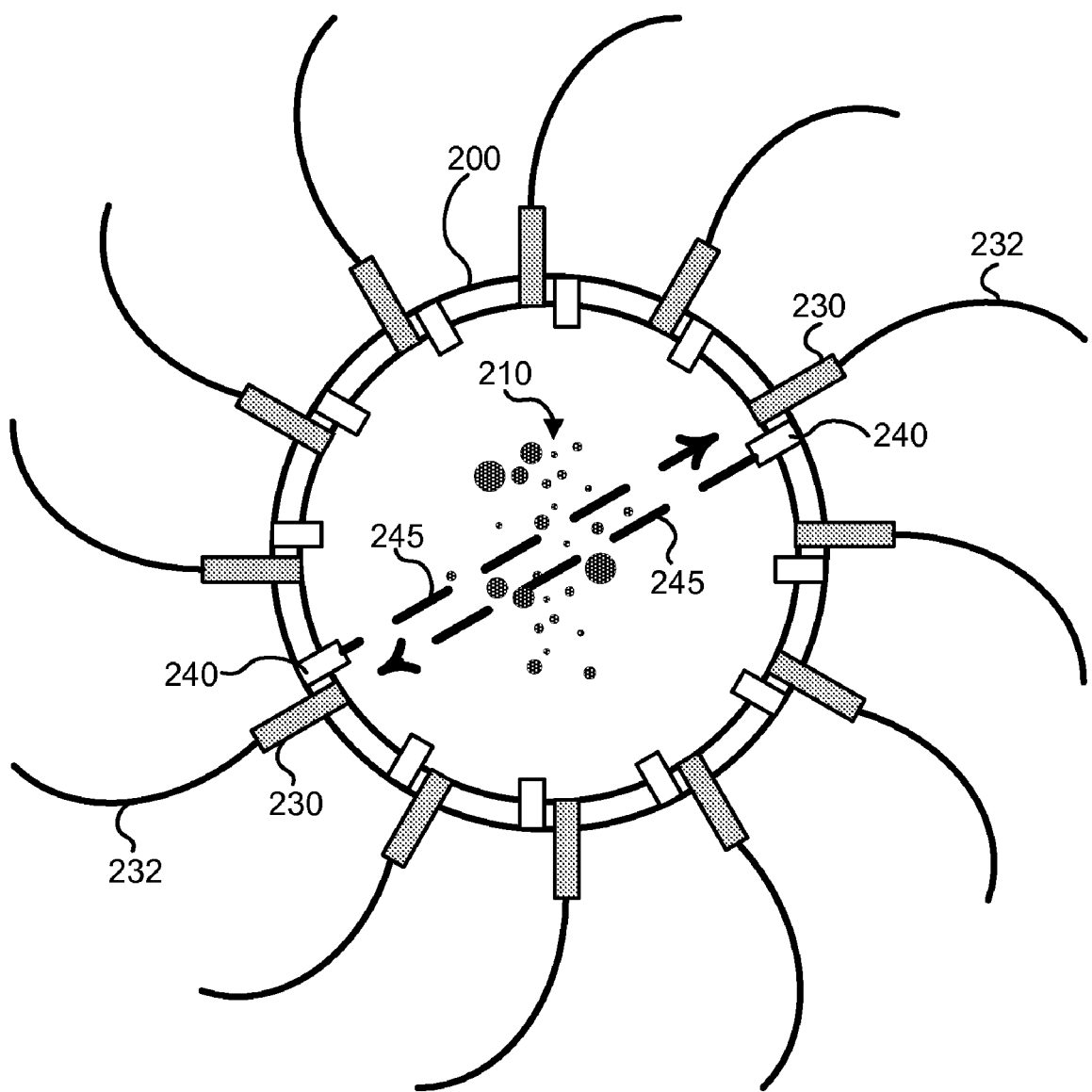
FIG. 2 is a depiction of a bulk material analyzer system according to an exemplary embodiment of the present invention.

FIG. 2 illustrates an end view of a bulk material analyzer system according to the present invention. The bulk material analyzer system is preferably implemented in a transport tube 200 through which a stream of bulk material 210 is transferred via a pneumatic system, air slide system, or otherwise. The system includes a plurality of probes 230 inserted within or through the transport tube 200. The probes 230 may be arranged approximately within a cross-section of the tube 200 that is perpendicular to a center axis (e.g., Z-axis) of the tube 200. For example, the probes 230 may be arranged, for example, in a planetary arrangement about a particular perimeter or circumference of the tube 200. The probes may alternatively be arranged in one or more helixes about the tube 200.

The probes 230 are preferably optical probes capable of detecting and/or receiving near infrared ("NIR") light. Each of the probes 230 are in communication with one or more NIR spectrometers (not shown) via optical fiber cables 232. In some other embodiments, the probes 230 are in wireless communication with the spectrometer (e.g., via a radio frequency link).

Located opposite each probe 230 is light source 240 (e.g., illuminator) for projecting light/radiation 245 towards the probe 230 and through the bulk material 210. Each light source 240 preferably provides sufficient illumination to encompass the full NIR range of 400 through 2500 nanometers (nm) in reflectant wave lengths. The light sources 240 may be adjusted between different intensities and frequencies, e.g., to enhance reflectance, emittance and absorptive optical phenomena resulting in discrete spectral signatures as light is reflected, emitted or absorbed providing characteristic and identifiable wavelengths. Each light source 240 may be mounted together with one of the probes 230, or separately mounted, in the tube 200.

Data from each probe 230, including data indicative of the frequencies of light and/or radiation received by the probe, is provided to the spectrometer to analyze and determine properties of the bulk material 210. As bulk material 210 passes by the probes 230, data can be taken continuously, in regular periods or on demand. The system measures the spectral signature of bulk materials 210 based on light that is reflected, emitted and absorbed by bulk materials 210. The system may then compare the spectral signature of each scan to a set of stored calibrations representing expected concentrations of previously characterized standards. This is done in real time with the help of computer software. As a result, the material characteristics of the bulk material distributed within the tube 200 is identified. The system also gathers the information of all scans to get the overall distribution of material within the scanned bulk material. Specific elements or their oxides can thereby be identified as to presence and characterized as to concentrations via intensities of detected and recognized spectral signatures. Interpretation and analysis of the data, and calibration of the system, is further described in commonly owned U.S. Patent Application Publication 2007/0263212, which is incorporated herein by reference.

Figure 3:
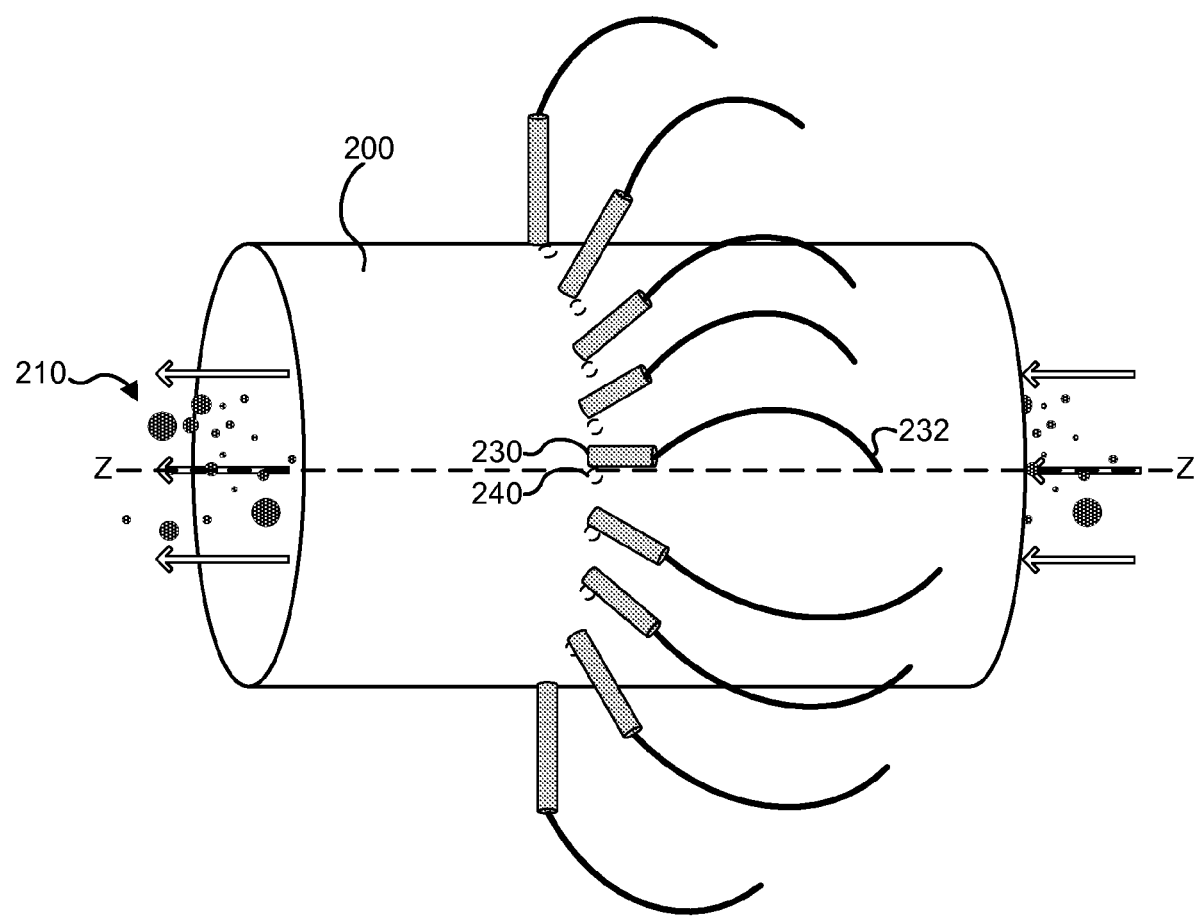
FIG. 3 is another depiction of the bulk material analyzer system according to an exemplary embodiment of the present invention.

FIG. 3 illustrates a side view of one exemplary embodiment of the bulk material analyzer system according to the present invention. A planetary arrangement of probes 230 and light sources 240, e.g., arranged approximately within a cross-section or a plane perpendicular the center axis, at a particular zone of the tube 200 is shown. In this arrangement, the probes 230 and light sources 240 are of any number sufficient to interrogate the full cross-section of the tube 200 material passing through the desired zone. The arrangement of probes 230 and light sources 240 may be implemented at one zone, or at a plurality of zones along the tube 200. Data pertaining to the bulk material 210 is transmitted from each of the probes 230 to the spectrometer.

Figure 4:
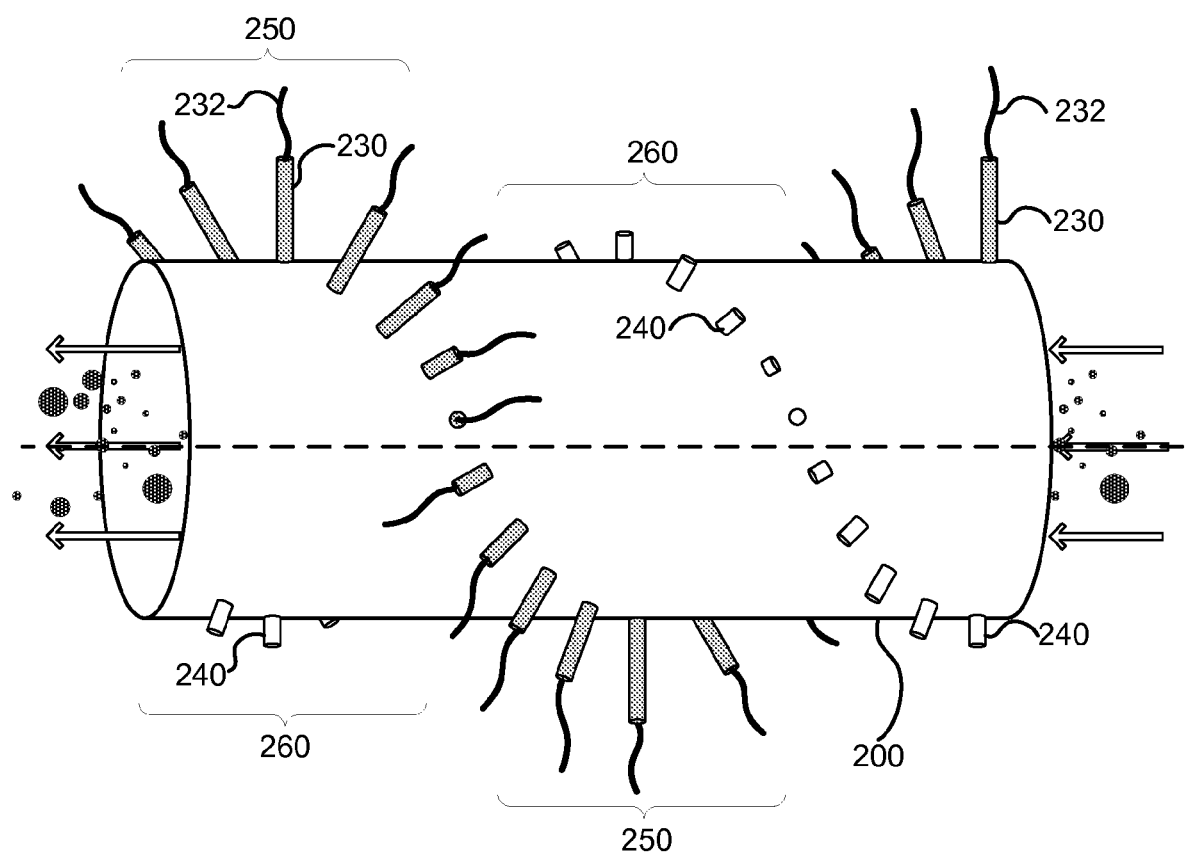
FIG. 4 is another depiction of the bulk material analyzer system according to an exemplary embodiment of the present invention.
Figure 5:
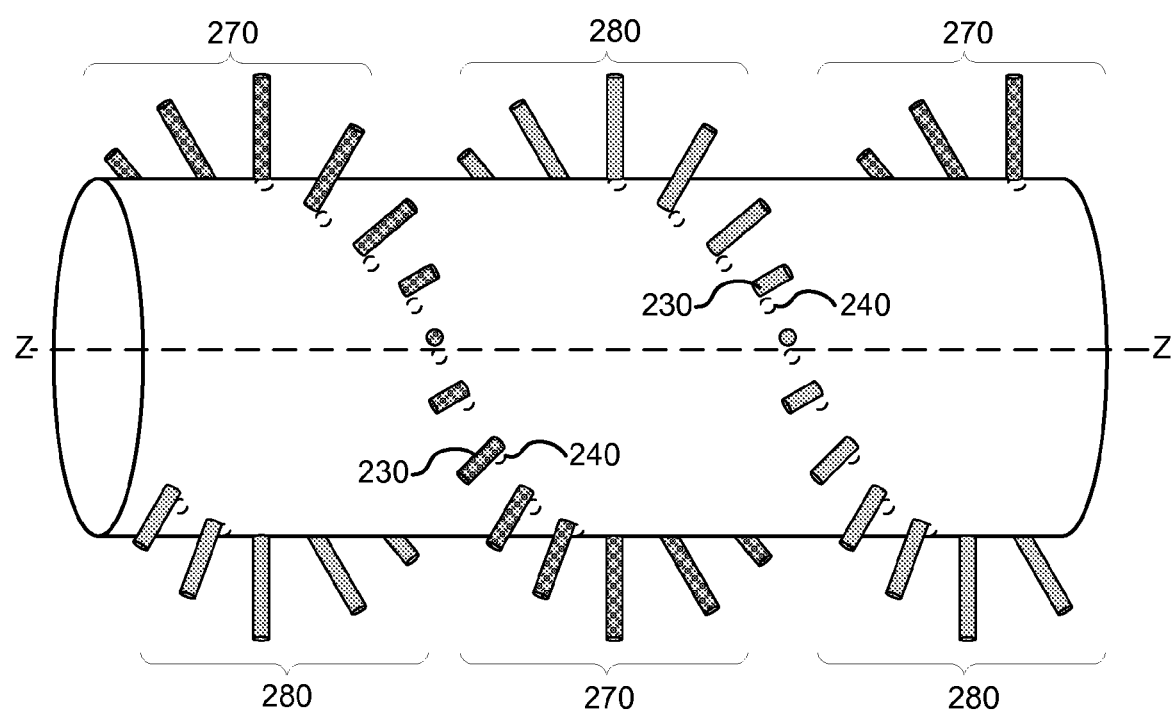
FIG. 5 is another depiction of the bulk material analyzer system according to an exemplary embodiment of the present invention.

In some embodiments, the probes 230 further extend in a helical arrangement along a distance of the tube 200. FIGS. 4 and 5 illustrate two such arrangements. It should be understood that FIGS. 4 and 5 illustrate only a portion of the system and tube 200. Helical arrangements may be implemented for any desired distance along a particular tube 200, or along multiple tubes 200.

In FIG. 4, the bulk material analyzer system includes a first helix 250 comprising a plurality of probes 230 extending along a distance of the tube 200. The system further includes a second helix 260, substantially opposite to the first helix 250, comprising a plurality of light sources 240 extending along the distance. The first and second helixes 250/260 preferably have the same direction or rotation about the tube 200. In the present embodiments, the first and second helixes are offset by approximately 180 degrees. Each of the probes 230 in the first helix 250 corresponds to and is substantially opposite a light source 240 in the second helix 260. By means of a helical arrangement, a full stream analysis of the pulverized bulk material 210 can be completely characterized.

FIG. 5 illustrates another exemplary arrangement of probes 230 and lights sources 240 according to the present invention. This particular arrangement includes a first helix 270 comprising a plurality of probes 230 and light sources 240. Each probe 230 is adjacent to, or integrated with, a light source 240. The arrangement further includes a second helix 280 also comprising a plurality of probes 230 and light sources 240. The first and second helixes 270/280 are substantially opposite one another such that each of the probes 230 in the first helix 270 is substantially opposite to a light source 240 in the second helix 280, and vice versa. Therefore, two probes 230 are arranged to collect data at any given point along the analyzed distance of the tube 200 to achieve a higher degree of accuracy.

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for analyzing a bulk material, comprising:
   a tube for transporting a stream of a bulk material;
   a plurality of illuminators for directing radiation through said stream and arranged about a circumference of said tube;
   a plurality of detectors arranged substantially opposite said illuminators; and
   at least one spectrometer for receiving and analyzing data from said plurality of detectors;
   wherein said plurality of detectors are arranged in a first helix extending along a length of said tube and said plurality of illuminators are arranged in a second helix extending along the length.

2. The system according to claim 1, wherein each of the plurality of detectors is arranged opposite of one of the plurality of illuminators.

3. The system according to claim 1, wherein each of said plurality of illuminators and each of said plurality of detectors are arranged substantially within a cross-section of said tube perpendicular to a center axis of said tube.

4. The system according to claim 1, further comprising:
   a further arrangement of a plurality of illuminators and a plurality of detectors arranged substantially within a further cross-section of said tube perpendicular to the center axis.

5. The system according to claim 1, wherein each of the first and second helixes extends in a same direction of rotation about said tube.

6. The system according to claim 5, wherein each of the first and second helixes are offset by about 180 degrees.

7. The system according to claim 1, wherein each of said plurality of illuminators is substantially adjacent to at least one of the detectors.

8. A system for analyzing a bulk material, comprising:
   a tube for transporting a stream of a bulk material;
   a plurality of illuminators for directing radiation through said stream and arranged about a circumference of said tube;
   a plurality of detectors arranged substantially opposite said illuminators;
   at least one spectrometer for receiving and analyzing data from said plurality of detectors;
   wherein each of said plurality of illuminators is substantially adjacent to at least one of the detectors; and
   wherein said plurality of detectors and said plurality of illuminators are arranged in two or more helical arrangements about said tube.

9. The system according to claim 8, wherein a first one of the two or more helical arrangements is substantially opposite a second one of the two or more helical arrangements.

10. The system according to claim 8, wherein each of the two or more helical arrangements extends in a same direction of rotation about said tube.

11. The system according to claim 10, wherein a first one of the two or more helical arrangements is offset by about 180 degrees from a second one of the two or more helical arrangements.

12. The system according to claim 1, wherein each of the plurality of detectors is connected to said spectrometer via an optical fiber.

13. The system according to claim 1, wherein each of said plurality of detectors is an optical near infrared probe.

14. The system according to claim 1, wherein each of said plurality of illuminators provides illumination within a range of about 400 nanometers to about 2500 nanometers.

15. The system according to claim 1, wherein the bulk material is a pulverized bulk material.

16. The system according to claim 1, wherein the bulk material includes cement.

17. The system according to claim 1, wherein said tube transports the bulk material from a first processing point to a second processing point.

18. The system according to claim 1, wherein the spectrometer provides information indicative of the composition of the bulk material in real time.

19. The system according to claim 1, wherein said stream of bulk material is projected via said tube by mean of one of an air slide and a pneumatic system.

20. A method for real-time analysis of a bulk material, comprising the steps of:
receiving a stream of a bulk material via a tube;
providing illumination across at least a portion of the stream via an array of illuminators arranged about a circumference of the tube;
receiving at least some of the illumination via plurality of detectors arranged substantially opposite of the illuminators; and
providing data indicative of the illumination received via the detectors to at least one spectrometer for analysis;
wherein the illuminators and detectors are arranged in two or more helical arrangements extending along a length of the tube.

21. The method according to claim 20, wherein the illumination is provided in one or more directions substantially perpendicular to a direction of the stream.

22. The method according to claim 21, wherein each illuminator is substantially adjacent to at least one detector about the circumference.

23. The method according to claim 20, further comprising the step of:
determining a composition of the bulk material at two or more positions along the length.

24. The method according to claim 20,
wherein the illuminators are arranged in a first helical arrangement extending along a length of the tube;
wherein the detectors are arranged in a second helical arrangement offset from the first helical arrangement by about 180 degrees and extending along the length.

25. The method according to claim 24, further comprising the step of:
determining a composition of the bulk material at two or more positions along the length.

26. The method according to claim 20, wherein the tube transports the bulk material from a first processing point to a second processing point.

27. The method according to claim 20, wherein each of the plurality of detectors is an optical near infrared probe.

* * * * *